(12) United States Patent
Kawaji et al.

(10) Patent No.: US 6,231,884 B1
(45) Date of Patent: May 15, 2001

(54) PLASTERS CONTAINING ISOSORBIDE DINITRATE

(75) Inventors: Toshikuni Kawaji; Masahiro Yamaji, both of Kagawa (JP)

(73) Assignee: Teikoku Seiyaku Co., Ltd., Kagawa (JP)

(*) Notice: Subject to any disclaimer, the term of this patent is extended or adjusted under 35 U.S.C. 154(b) by 0 days.

(21) Appl. No.: 09/214,763

(22) PCT Filed: May 11, 1998

(86) PCT No.: PCT/JP98/02062

§ 371 Date: Aug. 10, 1999

§ 102(e) Date: Aug. 10, 1999

(87) PCT Pub. No.: WO98/51299

PCT Pub. Date: Nov. 19, 1998

(30) Foreign Application Priority Data

May 12, 1997 (JP) .................................................. 9-135751

(51) Int. Cl.$^7$ ............................. A61F 13/00; A61F 13/02
(52) U.S. Cl. ........................... 424/443; 424/448; 424/449
(58) Field of Search .................................. 424/443, 449, 424/448

(56) References Cited

U.S. PATENT DOCUMENTS

| 4,537,776 | 8/1985 | Cooper . | |
|---|---|---|---|
| 5,413,794 | * 5/1995 | Suzuki et al. | 424/449 |
| 5,725,874 | * 3/1998 | Oda et al. | 424/443 |

FOREIGN PATENT DOCUMENTS

| 63-307818 | 12/1988 | (JP) . |
| 6-24969 | 2/1994 | (JP) . |

* cited by examiner

*Primary Examiner*—Thurman K. Page
*Assistant Examiner*—Isis Ghae
(74) *Attorney, Agent, or Firm*—Evenson, McKeown, Edwards & Lenahan, P.L.L.C.

(57) ABSTRACT

The present invention provides plasters containing an adhesive base material which comprise, by wt % of the adhesive base material, 15–25 wt % of isosorbide dinitrate, 15–35 wt % of styrene-isoprene-styrene block copolymer, 35–55 wt % of rosin resin, 5–20 wt % of liquid rubber, 0.1–2 wt % of antioxidant, and 0.1–5 wt % of oleic acid for transdermal application. The plasters of the present invention have excellent adhesion and stable releasing of the active ingredient from the adhesive layer after applied to the skin.

10 Claims, No Drawings

PLASTERS CONTAINING ISOSORBIDE DINITRATE

TECHNICAL FIELD

The present invention relates to the plasters for the treatment of the ischemic heart disease, and more specifically, to the plasters containing isosorbide dinitrate as an active ingredient.

BACKGROUND ART

Isosorbide dinitrate is nitrate compound widely used as medicine for the treatment of ischemic heart disease, especially as an antianginal drug. It is also used as raw materials for explosive. The pharmaceutical formulations of isosorbide dinitrate such as sublingual tablet for the internal use, injection or spray formulation have been proposed, and furthermore, various kinds of tapes such as sustained releasing transdermal formulation are also proposed.

Isosorbide dinitrate is the substance which melts at 77° C., and for the safety transportation, it is sold in 40% admixture powdery form with lactose. Therefore, to produce adhesive tapes containing isosorbite dinitrate, it has to be extracted from lactose admixture powdery form using organic solvent such as ethyl acetate, and the resulting organic solvent of isosorbite dinitrate is combined into the adhesive base materials. For the adhesive base material to be used for the tapes, solvent type of acrylic acid adhesive can be used. The solvent used for the acrylic acid adhesive may be the same one used for the extraction of isosorbide dinitrate, such as ethyl acetate.

However, there found to be problems such as crystallization of isosorbide dinitrate in the adhesive layer and the decreasing of adhesion when the ratio of isosorbide dinitrate of the base material is increased to achieve its high pharmaceutically effects. As a result, enough adhesion of the tapes to the skin and stable releasing of the active ingredient from the adhesive layer is not obtained.

Isosorbide dinitrate is a substance with sublimation and hygroscopic properties, and therefore, the conventional backings used for the transdermal formulation such as polyvinyl chloride film, polyester film or polypropylene film can not be used. The laminated backing composed of polyester film and another film were used for the transdermal preparation of isosorbide dinitrate; however, it was difficult to apply to the skin due to the thinness of the laminated backing.

DISCLOSURE OF THE INVENTION

This invention is made to solve the above mentioned problems and the purpose of the present invention is to provide the transdermal formulation containing isosorbide dinitrate as an active ingredient. More specifically, present invention is to provide plasters containing isosorbite dinitrate which possess the sufficient adhesion at the time of applying to the skin, and sustain stable releasing of the active ingredient from the adhesive layer.

The inventors of the present invention made intensive and extensive studies to solve the problems, and succeeded in finding that the adhesive base material with main component of styrene-isoprene-styrene block copolymer possesses excellent adhesion and efficient releasing of the ingredient from the adhesive base material at the same time.

Furthermore, the present inventors found that the laminated polyester film with non-woven fabrics can be used as the backings for the adhesive base material containing isosorbide dinitrate of the transdermal formulation to overcome these problems.

Therefore, one aspect of the present invention is to provide the plaster containing isosorbide dinitrate as an active ingredient in the adhesive base material which is composed of styrene-isoprene-styrene block copolymer, rosin resin, liquid rubber, antioxidant and oleic acid.

In a specific embodiment of the present invention, it is provided that the plasters containing isosorbide dinitrate which is comprised by mixing ethyl acetate solution of isosorbide dinitrate with the solvent-type adhesive base material consisting styrene-isoprene-styrene block copolymer, rosin resin, liquid rubber, antioxidant and oleic acid. And the resulting mixture is spread on the silicone treated liner and dried. Then, the obtained liner is laminated with the flexible backing.

In a more specific embodiment, the present invention provides the plasters containing isosorbide dinitrate in the adhesive base material composed of 15–35 w/w % (weight/weight percent: the same as hereinafter) of styrene-isoprene-styrene block copolymer, 35–55 w/w % of rosin resin, 5–20 w/w % of synthetic liquid rubber, 0.1–2 w/w % of antioxidant, and 0.1–5 w/w % of oleic acid.

In a preferred embodiment, the present invention provides the plasters containing isosorbide dinitrate with the amount of 15–25 w/w % in the adhesive base material.

In a more preferred embodiment of the present invention, the each components of adhesive base material may be hydrogenated rosin resin for the rosin resin, polybutene or high cis polyisoprene rubber as the liquid rubber, dibutyl-hydroxytoluene or pentaerythrityl-tetrakis [3-(3,5-di-t-butyl-4-hydroxyphenyl)] propionate as the antioxadant.

BEST MODE FOR CARRING OUT THE INVENTION

The components composed of the adhesive base material for the plasters of the present invention are described below to disclose the present invention in more detail.

The styrene-isoprene-styrene block copolymer used for the plasters of the present invention may be a synthetic liquid rubber. This synthetic rubber acts as basic framework of adhesive base material, and the one which is preferred for the purpose has ratio of styrene/rubber as 14/86. The amount of this synthetic rubber in the adhesive base material may be 15–35 w/w %, more preferably 20–30 w/w %.

When the amount of the synthetic rubber is less than 15 w/w %, aggregated strength of the adhesive base material can not be achieved and the adhesive base material may be likely to form unevenly. On the contrary, when the amount of the rubber is more than 35 w/w %, the adhesive base material becomes too stiff and the crystallization of the isosorbide dinitrate may occur due to the decrease of the amount of the other components, and therefore it is not preferred.

The rosin resin used for this invention may be hydrogenated rosin resin with light color, and this resin possesses wide range of solubility for another components, and excellent stability for heat and oxidation. The amount of this resin in the base material may be 35–55 w/w %, more preferably 40–50 w/w %.

When the amount of the resin is less than 35 w/w %, the adhesive base material may loose appropriate adhesive strength, and when it is more than 55 w/w %, the adhesive base material may become hard and the adhesive strength may decrease, and therefore it is not preferred.

The liquid rubbers to be used for the present invention may be polybutene or high cis polyisoprene rubber. The amount of this liquid rubber may be 5–20 w/w %, more preferably 7–15 w/w %. The liquid rubber of the present invention is used as a softener for the adhesive base material. When the amount of this rubber in the adhesive base material is less than 5 w/w %, softness of the base material may not be seen and therefore it is not preferred. Furthermore, if it is more than 20 w/w %, bleeding of the components from the adhesive base material may occur and it also is not preferred.

The antioxidant is essential component to stabilize the adhesive base material at the time of production and preservation period, and various kinds of antioxidant may be used. Among them, dibutyl-hydroxytoluene or pentaerythrityl-tetrakis [3-(3,5-di-t-butyl-4-hydroxyphenyl)] propionate is most preferable for the sake of safety standpoints, and the amount of the antioxidant in the adhesive base material may be 0.1–2 w/w %.

For the plasters of the present invention, oleic acid is used as the absorption accelerant and the amount of oleic acid in the adhesive base material may be 0.5–5 w/w %, more preferably 0.5–3 w/w %. When the amount of oleic acid is less than 0.5 w/w %, the expected absorption acceleration effect is not achieved, and with it more than 5 w/w %, aggregated strength of the adhesive base material decreases and no more increase in absorption acceleration effect is achieved. Therefore it is not preferred.

The amount of isosorbide dinitrate as the active ingredient of the present invention may vary to achieve the desired pharmaceutical effect on the treatment of ischemic heart disease through the transdermal absorption of isosorbide dinitrate after skin application. In a specific embodiment, the amount of isosorbide dinitrate in the adhesive base material may be 15–25 w/w %.

When the amount of isosorbide dinitrate is less than 15 w/w %, the whole volume of the adhesive layer of the plaster must be increased to gain sufficient effect of the active ingredient. As a result, drying process for the plaster takes a long time, and therefore, the production cost may be increased. On the other hand, when the amount of isosorbide dinitrate is more than 25 w/w %, the appearance of crystalline of this compound in the adhesive base material may immediately occur after the production of the adhesive base material, and therefore, it is not preferred.

From the above results, the preferred embodiment of the present invention is the plaster containing isosorbide dinitrate in the adhesive base material comprising 15–35 w/w % of styrene-isoprene-styrene block copolymer, 35–55 w/w % of rosin resin, 5–20 w/w % of liquid rubber, 0.1–2 w/w % of antioxidant, and 1–5 w/w % of oleic acid.

In more preferred embodiment, the present invention provides isosorbide dinitrate containing plaster which adhesive base material is composed of 20–30 w/w % of styrene-isoprene-styrene block copolymer, 40–50 w/w % of rosin resin, 7–15 w/w % of liquid rubber, 0.1–2 w/w % of antioxidant, and 0.5–3 w/w % of oleic acid.

Therefore, the most preferred embodiment of the present invention is the plaster containing 15–25 w/w % of isosorbide dinitrate in the above-mentioned adhesive base material.

The plaster of the present invention may be produced by using the amount of each component as stated above, and with the method described below.

The liquid rubber, antioxidant and oleic acid are mixed with solution of styrene-isoprene-styrene block copolymer in toluene (1:1) under heating, and then the mixture is well stirred. At the same time, rosin resin is added to ethyl acetate solution of isosorbide dinitrate, and the mixture is also well stirred. Later isosorbide dinitrate solution is combined with former styrene-isoprene-styrene block copolymer (toluene solution), and then the mixture is stirred to produce the adhesive base material.

Followed by the above procedure, the resulting adhesive base material is spread on the silicon treated liner with the conventional method, and the liner is dried to remove off the solvent. Then, the liner thus obtained is cut into desired size to produce the plaster of the present invention.

The amount of the adhesive base material to be spread on the liner may be 30–100 $g/cm^2$, preferably 40–80 $g/cm^2$ based on the plaster after drying.

The plasters containing isosorbide dinitrate of the present invention would be applied to the skin for a long period of time for treatment of ischemic heart disease. Therefore, the backing of the plaster is preferred to be flexible with no diffusion of the active ingredient, i.e., isosorbide dinitrate. Among the backing available, the heat laminated or adhered laminated backing of the woven or non-woven fabrics made from about 6–15 $g/cm^2$ in weight of rayon, vinylon or polyolefin, with polyester film (thickness: 2.5–6.0 $\mu$m) may be preferably used.

EXAMPLES

The present invention will be further illustrated by the following examples. It is to be understood that the present invention is not limited to these examples. The detail may be deleted, added, or substituted as it is deemed to be appropriate, so long as the pharmacological activities of the plaster of the present invention is not changed. Such changes are also covered within the technical scope of the present invention.

Examples No.1–No.8

By using the components stated in Table 1 below and the procedure mentioned above, each adhesive base materials was manufactured. The adhesive base materials thus obtained were spread on the silicon treated polyester liner so that the quantity of isosorbide dinitrate was 1 $mg/cm^2$ (after drying), and the resulting liner was left for 10 minutes at about 80° C. for drying. Then, the resultant liner was layered with the laminated backing composed of polyethylene telephthalate (PET) film having the thickness of 3.5 $\mu$m and 12 $g/m^2$ of non-woven fabric of vinylon, to produce the plasters of examples No.1–No.8.

TABLE 1

Prescription for the each Example

| Raw materials: Grade/Makers | Examples (w/w %) | | | | | | | |
|---|---|---|---|---|---|---|---|---|
| | No. 1 | No. 2 | No. 3 | No. 4 | No. 5 | No. 6 | No. 7 | No. 8 |
| Isosorbide dinitrate 20% ethyl acetate solution/Chugoku Kayaku Inc.: Solidity Indicator | 16 | 18 | 20 | 18 | 18 | 18 | 18 | 18 |
| Styrene-isoprene-styrene block copolymer: TR-1107/ Shell Chemicals Inc. | 30 | 25 | 30 | 20 | 25 | 30 | 30 | 30 |
| Glycerol ester of hydrogenated rosin: Super ester A-100/ Arakawa Chemical Industry Inc. | 40 | 46 | 40 | | | | | |
| Super hydrogenated rosin ester: KE-311/ Arakawa Chemical Industry Inc. | | | | 50 | 45 | 40 | 40 | 40 |
| Polybutene: HV-300/ Nippon Petero-chemicals Co., Ltd. | 12 | 9 | 8 | | | | | |
| High cis polyisoprene rubber LIR-50/ Kuraray Co., Ltd. | | | | 10 | 10 | 10 | 8 | 6 |
| Antioxidant (dibutyl hydroxytoluene) BHT/ Takeda Chemical Industries, Ltd. | 1 | 1 | 1 | 1 | 1 | 1 | 1 | 1 |
| Oleic acid: (JSCI)/ NOF Co. | 1 | 1 | 1 | 1 | 1 | 1 | 1 | 1 |

Comparative Example No.1

By using the components stated in Table 2 below and the substantially same manner described in the Examples above, the adhesive base material was manufactured, and the plaster of the Comparative Example No.1 was produced.

TABLE 2

Prescription for the Comparative Example No. 1 (w/w %)

| Raw materials: Grade/Maker | Comparative Example No. 1 |
|---|---|
| Isosorbide dinitrate 20% ethyl acetate solution / Chugoku Kayaku Inc.: Solidity Indicator | 18 |
| Styrene-isoprene-styrene block copolymer:TR-1107 / Shell Chemicals Inc. | 30 |
| Saturated fatty acid hydrocarbon Oil resin: Alcon P-100 / Arakawa Chemical Industry Inc. | 40 |
| High cis polyisoprene rubber LIR-50 / Kuraray Co., Ltd. | 11 |
| Antioxidant (dibutylhydroxytoluene) BHT / Takeda Chemical Industries, Ltd. | 1 |
| Oleic acid: (JSCI)/ Kuraray Co., Ltd. | 1 |

Comparative Example No.2

In 4 necked flask, 74.4 g of 2-ethylhexyl acrylate and 5.6 g of acrylic acid in ethyl acetate were polymerized by each other by the use of azoisobutyronitrile as polymerization initiator under nitrogen gas atmosphere at 60° C. After polymerization, ethyl acetate was added to the reaction mixture to produce acrylic acid type adhesive solution with 40% solidity. Then, 100 g of ethyl acetate solution of isosorbide dinitrate (20% solution) was added to this reaction mixture, and the mixture was stirred to obtain the adhesive base material. The resultant adhesive base material was spread on silicon treated polyester liner to be weighed 50 g/m$^2$after drying (1 mg/cm$^2$ as isosorbide dinitrate), and then dried for 10 minutes at 80° C. The liner thus obtained was layered with backing and cut into the desired size to produce the plaster of Comparative Example No.2.

Comparative Example No.3

By the substantially same manner as described in Comparative Example No.2, 59.2 g of 2-ethylhexyl acylylate, 4.8 g of acrylic acid, 16.0 g of vinyl acetate, and 20.0 g of isosorbide dinitrate were used to produce the plaster of Comparative Example No.3.

[Various Test Examples]

To demonstrate the usefulness of the present invention, in vitro skin permeability test, adhesive strength test, and crystallization from the adhesive base material test of the plasters of the present invention were conducted comparison to the plasters obtained in Comparative Examples.

Test 1: In Vitro Skin Permeability Test on Rats
Method:

The abdominal region of Wistar strain rats (male, 6 weeks old) was shaved with a hair dipper and a shaver, and the skin is taken out. The obtained skin was placed in the Frantz-type diffusion cell, and the each plasters (produced in Examples No.1–No.8 and Comparative Examples No.1–No.3) were applied on the skin. The physiological saline solution was used as a receptor solution, and the warm water of approximately 37° C. was circulated through the cell jacket.

The samples were taken out as the time passes, and the amount of isosorbide dinitrate permeated the skin were measured by using the HPLC method.

Results:

The total amount of isosorbide dinitrate from the each plaster through the skin 24 hours after the application was stated in Table 3 below.

TABLE 3

Result of In Vitro Skin Permeability Test on Rats

| Plasters (Example No.) | Permeated Amount ($\mu g/cm^2$) | Plasters (Comparative Example No.) | Permeated Amount ($\mu g/cm^2$) |
|---|---|---|---|
| No. 1 | 415 | No. 1 | 284 |
| No. 2 | 430 | No. 2 | 431 |
| No. 3 | 445 | No. 3 | 393 |
| No. 4 | 432 | | |
| No. 5 | 428 | | |
| No. 6 | 434 | | |
| No. 7 | 458 | | |
| No. 8 | 449 | | |

The foregoing results clearly demonstrate that the skin permeability of isosorbide dinitrate from the plasters of the Examples No.1–No.8 of the present invention were much superior to the plasters of the Comparative Examples.

Test 2: Adhesive Strength Test:

Method:

Each plaster (the plasters obtained in Examples No.1–No.8 and Comparative Examples No.1–No.3) was cut into 25 mm×100 mm in size, and the one corner side was strip off. Then the supporting paper (25 mm×120 mm) was pasted together in about 10 mm length of that corner side, and the liner was eliminated. The surface of Bakelite board (25 mm×120 mm) was washed with acetone, and the plaster was applied on the surface of the Bakelite board with 2 kg weight of rubber roller. After 1 hour, the supporting paper was held back, and the adhesion strength was measured using Pulling Tester with the speedvelocity of 300 mm/minute. The test was conducted under the condition of 23±2° C. in temperature.

Results:

The adhesion strength of the each plaster was stated in Table 4 below.

TABLE 4

Results of Adhesive Strength Test

| Plasters (Example No.) | Adhesive Strength (g/25 mm) | Plasters (Comparative Example No.) | Adhesive Strength (g/25 mm) |
|---|---|---|---|
| No. 1 | 1730 | No. 1 | 260 |
| No. 2 | 1820 | No. 2 | 424 |
| No. 3 | 1540 | No. 3 | 388 |
| No. 4 | 1790 | | |
| No. 5 | 1680 | | |
| No. 6 | 1490 | | |
| No. 7 | 1370 | | |
| No. 8 | 1270 | | |

The adhesive strength of the plaster of the present invention as in Examples No.1–No.8 is clearly stronger compared to the Comparative Examples, and not likely to fall off during the application to the skin for a long period.

Test 3: Crystallization Appearance Test:

Each plaster (the plasters obtained in Examples No.1–No.8 and Comparative Examples No.1–No.3) was placed in polyethylene-aluminum bag, and stored for 1 month at 4° C. After the storage period, the plaster was taken out and the appearance of crystalline of isosorbide dinitrate in the adhesive base material of the plaster was observed with optical microscope.

The result is stated in Table 5 below.

TABLE 5

Results of Crystallization Appearance Test

| Plasters (Example No.) | Appearance of crystalline | Plasters (Comparative Example No.) | Appearance of crystalline |
|---|---|---|---|
| No. 1 | None | No. 1 | Observed |
| No. 2 | None | No. 2 | Observed |
| No. 3 | None | No. 3 | Observed (a lot) |
| No. 4 | None | | |
| No. 5 | None | | |
| No. 6 | None | | |
| No. 7 | None | | |
| No. 8 | None | | |

As is clear from the result, there is no crystallization of isosorbide dinitrate occurring in the plaster of the present invention, but it occurred in every case in the plaster of the Comparative Example. Especially crystalline are confirmed in the plaster of the Comparative Example No.3.

From the above results, it is understood that the plasters of the present invention is not likely to crystallize isosorbide dinitrate for long period of storage time, and therefore, possess stable releasing of the active ingredient.

INDUSTRY APPLICABILITY

According to the present invention, there can be provided the plasters containing isosorbide dinitrate in the adhesive base material consisting of styrene-isoprene-styrene block copolymer, rosin resin, liquid rubber, antioxidant, and oleic acid. The plaster containing isosorbide dinitrate of the present invention possesses the stable releasing of the active ingredient and storage stability at the same time, and its adhesion is especially remarkable.

Accordingly, this invention provides the plaster containing isosorbide dinitrate as the plasters for the treatment of the ischemic heart disease, which would be appropriate to be applied for the long time period, and thus excellent in the medical result.

What is claimed is:

1. A plaster for treating an ischemic heart disease containing an adhesive base material consisting of isosorbide dinitrate, styrene-isoprene-styrene block copolymer, rosin resin, liquid rubber, antioxidant, and oleic acid wherein the amount of isosorbide dinitrate is 15 to 25 w/w % based on the adhesive base material.

2. A plaster for treating an ischemic heart disease containing an adhesive base material consisting of isosorbide dinitrate, styrene-isoprene-styrene block copolymer, rosin resin, liquid rubber, antioxidant and oleic acid.

3. The plaster containing isosorbide dinitrate claimed in claim 1, in which the adhesive base material comprises 15–35 w/w % of styrene-isoprene-styrene block copolymer, 35–55 w/w % of rosin resin, 5–20 w/w % of liquid rubber, 0.1–2 w/w % of antioxidant, and 0.1–5 w/w % of oleic acid based on the adhesive base material.

4. The plaster containing isosorbide dinitrate claimed in claim 1, in which the adhesive base material comprises 20–30 w/w % of styrene-isoprene-styrene block copolymer, 40–50 w/w % of rosin resin, 7–15 w/w % of liquid rubber, 0.1–2 w/w % of antioxidant, and 0.1–3 w/w % of oleic acid based on the adhesive base material.

5. The plaster containing isosorbide dinitrate claimed in any one of claims 1 to 3, in which the rosin resin is hydrogenated rosin resin.

6. The plaster containing isosorbide dinitrate claimed in any one of claims 1 to 3, in which the liquid rubber is polybutene rubber or high cis polyisoprene rubber.

7. The plaster containing isosorbide dinitrate claimed in any one of claims 1 to 3, in which the antioxidant is dibutylhydroxytoluene or pentaerythrityl-tetrakis[3-(3,5-di-t-butyl-4-hydroxyphenyl)]propionate.

8. The plaster containing isosorbide dinitrate claimed in claim 4, in which the rosin resin is hydrogenated rosin resin.

9. The plaster containing isosorbide dinitrate claimed in claim 4, in which the liquid rubber is polybutene rubber or high cis polyisoprene rubber.

10. The plaster containing isosorbide dinitrate claimed in claim 4, in which the antioxidant is dibutylhydroxytoluene or pentaerythrityl-tetrakis [3-(3,5-di-t-butyl-4-hydroxyphenyl)]propionate.

* * * * *